United States Patent
Doan et al.

[11] Patent Number: 5,456,708
[45] Date of Patent: Oct. 10, 1995

[54] ROTATABLE PIN, SCREW-IN PACING AND SENSING LEAD HAVING IMPROVED TIP AND FLUIDIC SEAL

[75] Inventors: Phong D. Doan, Stevenson Ranch, Calif.; John R. Helland, Redmond, Wash.

[73] Assignee: Pacesetter, Inc., Sylmar, Calif.

[21] Appl. No.: 145,052

[22] Filed: Oct. 28, 1993

[51] Int. Cl.⁶ .................................................. A61N 1/04
[52] U.S. Cl. .................................................. 607/127
[58] Field of Search .................. 128/642; 607/115, 607/116, 122, 123, 125–128

[56] References Cited

U.S. PATENT DOCUMENTS

| | | |
|---|---|---|
| Re. 32,227 | 8/1986 | Dutcher . |
| 4,106,512 | 8/1978 | Bisping . |
| 4,146,036 | 3/1979 | Dutcher et al. . |
| 4,209,019 | 6/1980 | Dutcher et al. . |
| 4,217,913 | 8/1980 | Dutcher . |
| 4,233,992 | 11/1980 | Bisping . |
| 4,282,885 | 8/1981 | Bisping . |
| 4,311,153 | 1/1982 | Smits . |
| 4,350,169 | 9/1982 | Dutcher et al. . |
| 4,357,946 | 11/1982 | Dutcher et al. . |
| 4,463,765 | 8/1984 | Gold . |
| 4,624,266 | 11/1986 | Kane ........................................ 607/127 |
| 4,628,943 | 12/1986 | Miller . |
| 4,667,686 | 5/1987 | Peers-Traverton ...................... 607/127 |
| 4,799,499 | 1/1989 | Bisping . |
| 4,819,661 | 4/1989 | Heil, Jr. et al. . |
| 4,886,074 | 12/1989 | Bisping . |
| 4,953,564 | 9/1990 | Berthelsen . |
| 4,967,766 | 11/1990 | Bradshaw ............................ 128/642 X |
| 4,972,848 | 11/1990 | Di Domenico et al. . |
| 5,002,067 | 3/1991 | Berthelsen et al. . |
| 5,097,843 | 3/1992 | Soukup et al. . |

Primary Examiner—Lee S. Cohen
Assistant Examiner—Jeffrey R. Jastrzab
Attorney, Agent, or Firm—Malcolm J. Romano; Lisa P. Weinberg

[57] ABSTRACT

A rotatable pin, screw-in type lead assembly includes a radiopaque element proximate the distal tip of the lead assembly for permitting direct, rapid fluoroscopic verification of the amount of extension of the helix electrode relative to the tip. The radiopaque element is preferably in the form of a metallic ring having a porous, tissue-engaging outer surface which promotes rapid tissue ingrowth and consequent lead stabilization. The lead assembly further includes a low friction seal assembly operatively associated with a shaft carrying the helix electrode. The seal assembly reduces the number of turns of the lead assembly connector pin required to effect lead fixation or removal.

5 Claims, 1 Drawing Sheet

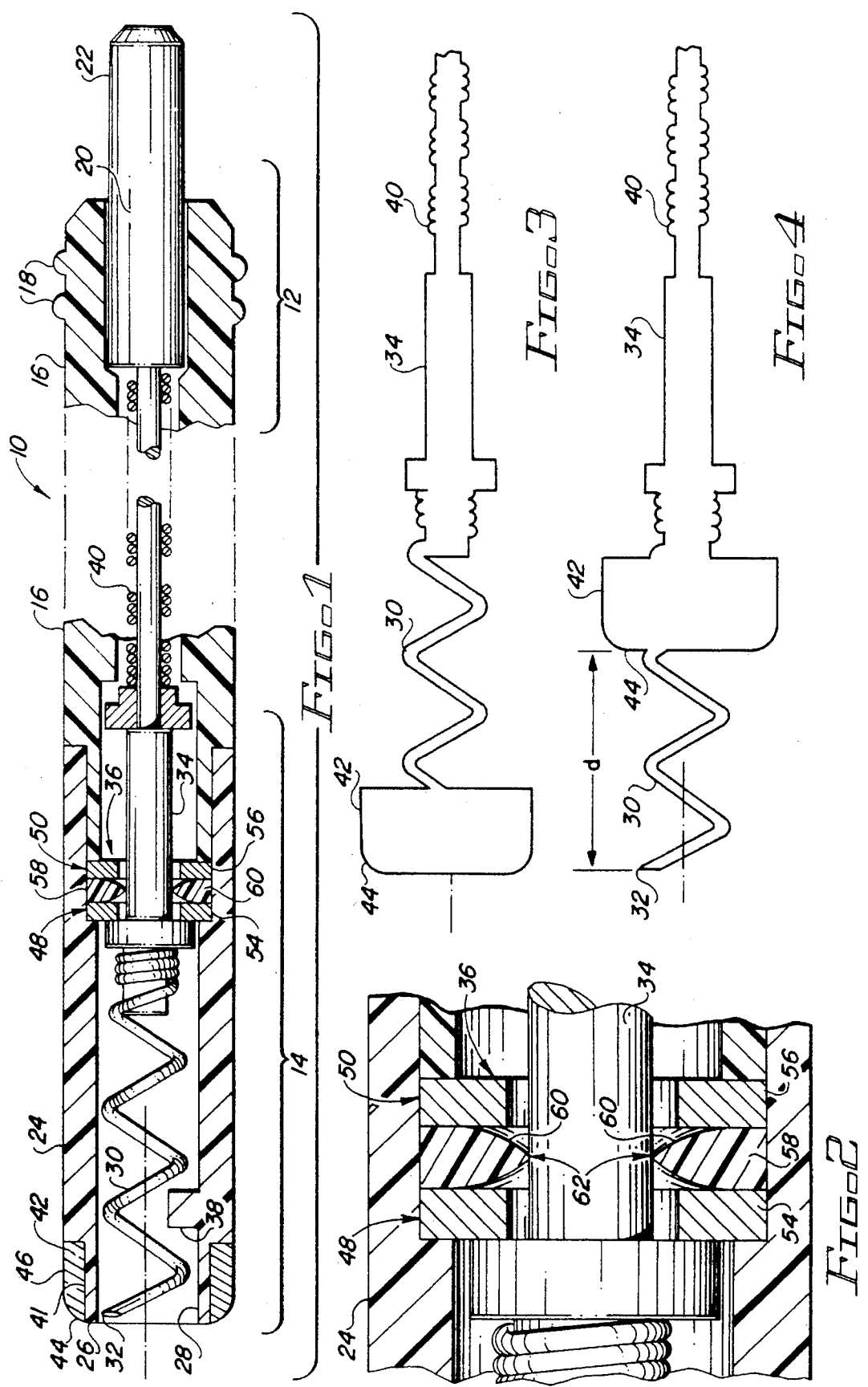

ROTATABLE PIN, SCREW-IN PACING AND SENSING LEAD HAVING IMPROVED TIP AND FLUIDIC SEAL

FIELD OF THE INVENTION

The present invention relates generally to implantable medical devices for providing stimulating pulses to selected body tissue and, more particularly, to the lead assemblies connecting such devices with the tissue to be stimulated.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. The appended claims are not intended to be limited, however, to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing or for sensing electrical signals produced by the heart, or for both pacing and sensing, in which case, a single lead serves as a bidirectional pulse transmission link between the pacemaker and the heart. An endocardial type lead, that is, a lead which is inserted into a vein and guided therethrough into a cavity of the heart, includes at its distal end an electrode designed to contact the endocardium, the tissue lining the inside of the heart. The lead further includes a proximal end having a connector pin adapted to be received by a mating socket in the pacemaker. A flexible, coiled conductor surrounded by an insulating tube or sheath couples the connector pin at the proximal end and the electrode at the distal end.

To prevent displacement or dislodgment of the electrode and to maintain the necessary stable electrical contact between the lead tip and the endocardial tissue, the electrode must be firmly anchored relative to the tissue. To achieve this, the electrode of one known type of lead comprises a pointed helix adapted to be screwed into the heart tissue to be stimulated. Rotational torque applied to the connector pin at the proximal end of the lead is transmitted via the flexible, coiled conductor to the helical electrode which is thereby screwed into the heart tissue. In this fashion, the position of the electrode tip is sought to be mechanically stabilized by positively anchoring the tip so that it remains securely in place during the lifetime of the implant. Removal of the screw-in electrode from the endocardium can be effected by counterrotation of the connector pin. Thus, in a rotatable pin, screw-in lead, the conductor coil is used not only as a conductor for electrically coupling the connector pin and the helix electrode, but also as a tool for extending or retracting the helix electrode relative to the distal tip of the lead during lead myocardium fixation by rotating the connector pin.

One problem associated with rotating pin, screw-in type leads is the inability to easily verify the degree of extension of the helix electrode relative to the lead tip especially where the distal end portion of the lead assembly comprises an insulating tubular housing of polyurethane or the like that is not readily visible on a fluoroscope. Present approaches to helix extension verification are not altogether satisfactory. For example, U.S. Pat. Nos. 4,953,564; 4,972,848; and 5,002,067 disclose screw-in type cardiac pacing leads in which the helix electrode is secured to the coiled conductor by means of a crimping sleeve. A narrow, radiopaque indicator ring is disposed within the lumen of the electrode head behind the lead tip. According to the aforementioned patents, by fluoroscopically observing the distance between the crimping sleeve and the indicator ring, the distance that the helix has been extended can be determined. The separation between the crimping sleeve and the indicator ring cannot always be readily ascertained, however, because of the presence in the viewing area of other metallic elements, such as the crimping core and coiled conductor, which tend to obscure the relative positions of the sleeve and ring. This is especially a problem when the pacing lead tip is being viewed at an angle relative to the plane of the fluoroscopic image. Moreover, even under the best fluoroscopic viewing conditions, because the pacing leads of the aforementioned patents furnish only an indication of the distance between the crimping sleeve and a ring that is positioned behind the lead tip, they do not provide a direct indication of the extension of the helix relative to the pacing lead tip.

Accordingly, it is an object of the invention to provide a rotatable pin, screw-in type lead assembly, for use with an implantable medical device that permits direct and rapid fluoroscopic verification of the degree of helix electrode extension from the distal tip of the lead assembly.

Another problem associated with the type of leads under consideration is that despite the anchoring provided by the helix electrode, the position of the tips of screw-in type leads relative to the heart tissue is often unstable. This mechanical instability can produce excessive trauma and inflammatory tissue reaction resulting in an increase in the stimulation threshold of the heart.

It is thus another object of the invention to provide a rotatable pin, screw-in type lead assembly, for use with an implantable medical device, having a tip structure that promotes rapid lead tip stabilization after fixation so as to reduce myocardium damage and the associated inflammatory response, and the associated peak and chronic stimulation thresholds.

In screw-in type leads, a seal is typically provided between the outer insulating tube and the helix electrode (or the shaft carrying the helix electrode) to prevent blood or other bodily fluids from entering the lead body. The friction between the helix electrode or shaft and the seal is a factor determining the torque and therefore the number of turns required to fully extend and retract the helix electrode during lead fixation. It is desirable to minimize such friction and thus the number of revolutions of the lead connector pin required to fully extend or retract the helix electrode so that lead fixation can be effected both expeditiously and with minimum displacement of the tip relative to the fixation location. Presently available screw-in type leads, however, often require an excessive number of revolutions of the lead connector pin to extend and retract the helix as a result of high frictional forces between the helix and the fluidic seal.

Thus, it is yet another object of the present invention to provide a screw-in lead assembly in which friction between the helix and fluidic seal, and hence the torque and number of connector pin turns required to extend and retract the helix electrode, is substantially reduced.

SUMMARY OF THE INVENTION

In accordance with one aspect of the present invention, there is provided an implantable flexible lead assembly of the rotatable pin, screw-in type having a helix electrode for piercing the tissue to be stimulated and including a distal tip for engaging the body tissue to be stimulated. A radiopaque ring is provided at the distal tip of the lead to facilitate rapid and accurate fluoroscopic verification of the extension of the helix electrode relative to the lead tip during lead fixation. The radiopaque ring has a porous outer surface which promotes rapid myocardium tissue ingrowth immediately after lead fixation. In this fashion, the tip of the lead is quickly stabilized, thereby minimizing myocardium damage and inflammatory reaction, and reducing the stimulation threshold. The ring may be fabricated of a biocompatible, biostable metallic material such as a platinum/iridium alloy with the porous surface being formed by metallic particles sintered to the outer surface of the ring.

Pursuant to yet another aspect of the invention, the helix electrode is mounted on a shaft operatively associated with a fluidic seal assembly for preventing the ingress of bodily fluids into the lead body. The seal assembly includes a washer-like seal element including an inner portion tapered to a small, low friction shaft contact area. The seal element is made of a biocompatible, biostable polymeric material such as polyurethane or silicone rubber and is sandwiched between a pair of longitudinally spaced-apart metallic washers. The combination of the seal element material and the small contact area between the seal element and the helix electrode shaft minimizes the frictional resistance between the shaft and seal element thereby reducing the number of turns of the connector pin required for fixation and removal of the helix electrode. Thus, fixation may be effected both expeditiously and with minimum displacement of the tip relative to the fixation location which might otherwise occur if friction levels were higher.

The various aspects of the present invention have general utility, being applicable to unipolar, bipolar and multipolar pacing and sensing leads as well as to a variety of implantable medical devices utilizing pulse generators to stimulate selected body tissue.

BRIEF DESCRIPTION OF THE DRAWINGS

Further objects, features and advantages of the invention will become apparent from the following detailed description of the preferred embodiment when read in conjunction with the accompanying drawings in which:

FIG. 1 is a longitudinal cross section view, in somewhat schematic form, of a unipolar rotatable pin, screw-in type lead assembly in accordance with the invention;

FIG. 2 is an enlarged view of the tapered seal shown in FIG. 1.

FIG. 3 is a diagrammatic representation of a fluoroscopic display image of the lead assembly of FIG. 1 with the helix electrode fully retracted; and FIG. 4 is a diagrammatic representation like that of FIG. 3 with the helix electrode fully extended.

DETAILED DESCRIPTION OF THE PREFERRED EMBODIMENTS

The following description presents several preferred embodiments representing the best mode contemplated for practicing the invention. This description is not to be taken in a limiting sense but is made merely for the purpose of describing the general principles of the invention whose scope is defined by the appended claims.

Referring to FIG. 1, there is shown a unipolar screw-in pacing and sensing lead assembly 10 having a proximal end 12, a distal end 14 and a tubular, insulating housing 16, made of an insulating biocompatible, biostable material such as polyurethane or silicone rubber, connecting the ends 12 and 14. The proximal end 12 is adapted to be plugged into a receptacle in a cardiac pacemaker (not shown), and for this purpose the housing 16 includes annular ribs 18 for sealing the pacemaker receptacle against the entry of bodily fluids. The tubular housing 16 encloses a generally cylindrical, rotatable connector pin 20 having a portion 22 projecting from the proximal end of the housing 16. The pin portion 22 is adapted to be received by a pacemaker socket coupled to the pulse generating and pulse sensing circuits within the pacemaker.

The distal end 14 of the lead 10 includes an elongated, tubular sheath or header 24 of polyurethane or like biocompatible, biostable insulating material having a distal tip surface 26 defining a central opening 28. The distal end 14 of the lead further encloses a rotatable, extendable/retractable helix electrode 30 having a sharp end 32 adapted to pierce the endocardial tissue. As is well known, the helix electrode 30 serves both as a fixation means to securely anchor the distal end 14 of the lead relative to the tissue to be stimulated and as an electrically conductive contact element for transmitting electrical stimulation and sensed pulses. The helix electrode 30 may be made of a platinum-iridium alloy or a similar biocompatible metal or metallic alloy. In FIG. 1, the helix electrode 30 is shown fully retracted within the distal end portion 14 of the lead in which position the sharp end 32 of the helix electrode is approximately in alignment with the tip surface 26.

The helix electrode 30 is carried by a shaft 34 laser welded or otherwise secured to the proximal end of the electrode 30. The helix shaft 34, in turn, is carried by a fluid-tight seal assembly 36, the helix shaft 34 being rotatably and axially movable relative to the seal assembly.

Projecting inwardly from the inner wall of the tubular header 24 proximate the tip 14 is a post 38 interposed between adjacent turns of the helix electrode 30. In this fashion, rotation in one direction or the other of the helix electrode 30 will cause the helix electrode 30 to be extended or retracted relative to the tip surface 26.

The helix shaft 34 is electrically and mechanically coupled to the rotatable connector pin 20 by means of a flexible conductor coil 40 housed within the insulating tube 16. It will thus be seen that given the helical sense of the electrode 30 as illustrated in FIG. 1, rotation of the connector pin 20 and conductor coil 40 in a clockwise direction (as viewed from the proximal end of the lead) will cause advancement of the helix electrode and its extension relative to the tip surface 26 to a fully extended position, while rotation of the connector pin 20 in a counterclockwise direction will result in retraction of the helix electrode 30 to its fully retracted position shown in FIG. 1.

Mounted within a recess 41 about the outer periphery of the elongated insulative header tube 24 adjacent the lead tip surface 26 is a ring 42 of platinum/iridium 90/10 or 80/20 alloy or similar biocompatible metal or metallic alloy. The ring 42, which may be machined to shape, is electrically isolated and is secured to the header tube 24 by means of a bonding agent such as a urethane adhesive. The ring 42 has an end surface 44 that is substantially contiguous with the tip surface 26. The ring 42 further has an outer surface 46, substantially flush with the outer surface of the tubular housing 16, and having a permeable or porous texture. Preferably, the desired porosity of the outer surface 46 of the ring 42 is provided by sintering platinum particles on the outer surface 46; this may be achieved by conventional sintering techniques.

The porous surface 46 of the ring 42 promotes rapid myocardium tissue ingrowth right after lead implant so as to quickly stabilize the tip of the lead to minimize myocardium damage or inflammatory reaction as well as the resulting stimulation threshold.

The metallic ring 42 is radiopaque and therefore visible fluoroscopically. By placing the ring 42 at the distal end of the insulative header tube 24, the ring produces a distinct fluoroscopic image with the distal end surface 44 thereof clearly visible. Accordingly, the extension of the helix electrode 30 relative to the tip surface 26 can be directly ascertained during lead fixation.

FIGS. 3 and 4 are representations of fluoroscopic displays of the distal end portion 14 of the lead assembly of the invention. The helix electrode 30, ring 42, helix shaft 34 and other metallic lead assembly elements are clearly visible. FIG. 3 shows the electrode 30 in its fully retracted position relative to the end surface 44 of the ring 42 which surface is in alignment with the less visible lead tip surface 26. FIG. 4 shows the electrode 30 extended a distance d from the ring end surface 44. The ability to thereby accurately and rapidly verify helix electrode extension relative to the tip of the lead assures proper and expeditious lead fixation.

As already explained, the number of turns of the connector pin 20 required to fully extend or fully retract the helix electrode is a function of several factors among which is the friction between the helix electrode (or helix electrode shaft) and the fluidic seal. It has been found that such friction, and therefore the number of turns required for full extension or retraction of the helix electrode, can be substantially reduced by means of the structure and geometry of the seal assembly 36 in accordance with another aspect of the invention. Thus, once the site of lead fixation has been determined, fixation is effected both expeditiously and with minimum displacement of the tip relative to the fixation location which might otherwise occur if friction levels were higher.

The seal assembly 36 is mounted between facing transverse, annular surfaces 48 and 50; the transverse surface 48 is defined by the header tube 24, while the transverse surface 50 comprises the distal end of the insulating tubular housing 16 a reduced diameter portion 52 of which is received by the proximal end of the header tube 24. The seal assembly 36 comprises a pair of spaced-apart washers 54 and 56 sandwiching an annular seal element 58. As best seen in FIG. 2, the seal element 58 has an inner portion 60 that, in cross-section, is tapered to a small, circular sealing contact area 62. The radius of the circular contact area 62 is such as to provide a light interference fit between the seal element 58 and the helix shaft 34. The seal element 58 may be fabricated of silicone rubber, polyurethane or any other biocompatible, biostable polymer. The combination of such a material and the small contact area between the seal element 58 and shaft 34 minimizes the frictional resistance between the shaft and seal thereby reducing the number of turns of the connector pin 20 required for fixation and removal of the helix electrode. The washers 54 and 56 are preferably fabricated of metal such as, for example, platinum or a platinum/iridium alloy or MP-35N alloy (nickel/cobalt/molybdenum).

Although the present invention has been described in terms of unipolar pacing and sensing lead assemblies it will be appreciated that the invention is applicable as well to bipolar leads having two conductors, and to multipolar leads employing multiple conductor leads including those incorporating a shock electrode.

What is claimed is:

1. An implantable flexible lead assembly adapted to transmit electrical pulses between a proximal end of the lead assembly and a distal end of the lead assembly and to thereby stimulate selected body tissue, the lead assembly including:

a helix electrode for engaging the selected body tissue;

a tubular, insulating housing extending between the proximal and distal ends of the lead assembly, the tubular housing including a header having a distal tip surface, the header further including means for causing the helix electrode to extend and retract relative to the distal tip surface upon rotation of the helix electrode;

a conductor coil extending between the proximal and distal ends of the lead assembly for transmitting the pulses, the conductor coil having a proximal end and a distal end, the conductor coil being adapted to rotate the helix electrode through rotation of the proximal end of the conductor coil;

a helix shaft coupling the distal end of the conductor coil and the helix electrode; and a seal operatively associated with the helix shaft for preventing the ingress of bodily fluids, said seal comprising a washer-like element including an inner portion tapering to a small, low friction contact area.

2. The lead assembly, as defined in claim 1, in which:

the seal is sandwiched between a pair of longitudinally spaced-apart washers.

3. The lead assembly, as defined in claim 2, in which:

the seal is made of a biocompatible, biostable polymeric material; and the washers are made of a biocompatible, biostable metallic material.

4. An implantable stimulation lead assembly adapted to transmit electrical pulses between a proximal and a distal end of the lead assembly and to thereby stimulate selected body tissue, the lead assembly including:

screw-in electrode means for engaging the selected body tissue;

a tubular, insulating housing extending between the proximal and distal ends of the lead assembly, the tubular housing including a distal end having a distal tip surface, the distal end further including means for causing the screw-in electrode means to extend and retract relative to the distal tip surface upon rotation of the screw-in electrode means;

a conductor coil extending between the proximal and distal ends of the lead assembly, the conductor coil having a proximal end and a distal end, the conductor coil being adapted to rotate the screw-in electrode means through rotation of the proximal end of the conductor coil;

a shaft coupling the conductor coil and the screw-in electrode means; and sealing means, encircling the shaft, for preventing the ingress of bodily fluids.

5. The lead assembly, as defined in claim 4, in which the sealing means comprises:

a washer-like seal made of a biocompatible, biostable polymeric material, the washer-like seal having an inner portion tapering to a small, low friction contact area; and a pair of longitudinally spaced-apart washers, the washer-like seal being sandwiched between the pair of longitudinally spaced-apart washers.

* * * * *